Aug. 12, 1975 N. KEEFER Plant Pat. 3,761
POINSETTIA PLANT
Filed June 20, 1974
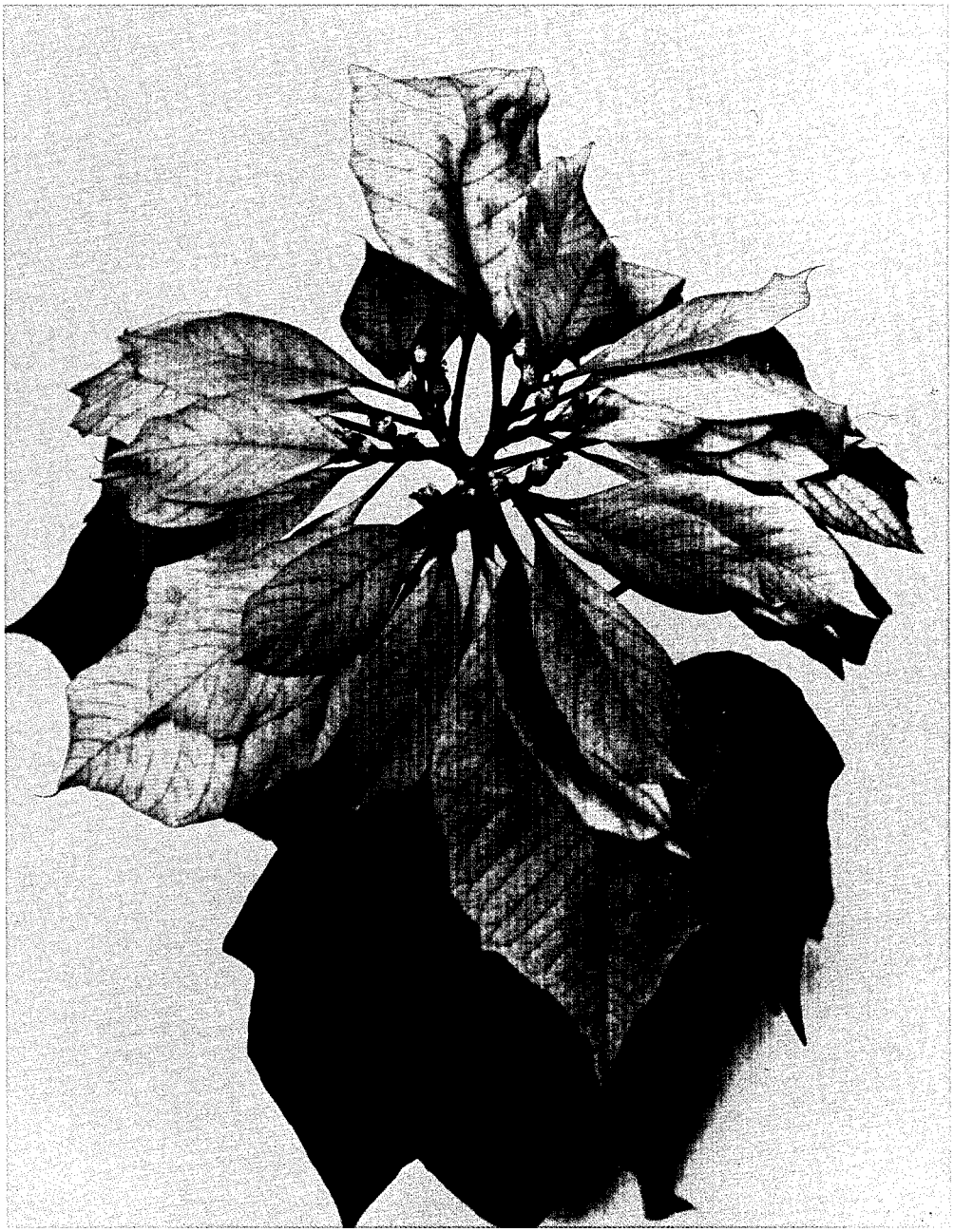

United States Patent

Plant Pat. 3,761
Patented Aug. 12, 1975

3,761
POINSETTIA PLANT

Ned Keefer, Andrews, Ind., assignor to Paul Ecke, Jr., Encinitas, Calif.

Filed June 20, 1974, Ser. No. 481,453
Int. Cl. A01h *5/00*
U.S. Cl. Plt.—86 1 Claim

The present invention relates to a new and distinct variety of poinsettia plant, botanically known as *Euphorbia pulcherrima,* which was discovered by me as a cultivated sport of the poinsettia variety known as "Dark Red Annette Hegg" (U.S. Plant Pat. No. 3,160), said discovery having been made by me in my greenhouse at Andrews, Ind.

At the time of my discovery aforesaid, I was growing various poinsettia varieties, including many plants of the variety "Dark Red Annette Hegg." During these growing operations, which were being conducted under my personal supervision and care, my attention was attracted to one particular plant among those of "Dark Red Annette Hegg" which bore dark pink bracts instead of the normal dark red bracts of "Dark Red Annette Hegg." Close inspection of this particular plant showed that it had sported, and I accordingly took steps to carefully preserve the sport and keep it under close observation. In due course, I also asexually reproduced the sport by vegetative cuttings taken therefrom and grown by me in my greenhouse at Andrews, Ind. Continued observations and tests of the original sport and its progeny derived therefrom as aforesaid, established and confirmed that the dark pink bract color comes true and remains stable through succeeding propagations. Otherwise, the new sport is substantially identical in all respects to the variety "Dark Red Annette Hegg." This has been further confirmed by extensive tests and observations conducted on my behalf at Encinitas, Calif. I am, therefore, convinced that my new dark pink-bracted sport represents a new and distinct poinsettia variety as evidenced by the following unique combination of characteristics which are outstanding therein and which distinguish the same from its parent, as well as from all other poinsettia varieties of which I am aware:

(1) A general similarity in most respects to the variety "Dark Red Annette Hegg," including
(2) A short growing and compact plant habit;
(3) A uniform and fast rooting habit;
(4) A self-branching habit which produces multiple blooms without pinching off the terminal buds;
(5) Attractive green foliage;
(6) Distinctive, attractive and stable dark pink bracts instead of dark red bracts like the "Dark Red Annette Hegg"; and
(7) Long-lasting plant qualities.

The accompanying drawing shows a typical specimen plant of my new poinsettia variety as illustrated in color.

Although, except for the bract color, the details of the new variety substantially conform to the description embodied in U.S. Plant Pat. No. 3,160, to which reference may be readily had, the following brief description is given for convenience, with color terminology in accordance with Wilson's Horticultural Colour Chart, except where general color terms of ordinary dictionary significance are obvious:

LOCALITY WHERE GROWN AND OBSERVED: Andrews, Ind., and also Encinitas, Calif., U.S.A.
PARENTAGE: Sport of "Dark Red Annette Hegg."
PROPAGATION: Holds its distinguishing characteristics through succeeding propagations by vegetative cuttings.
FORM: Short growing; compact.
HABIT OF GROWTH: Self-branching; contrary to other poinsettia varieties, does not require pinching off terminal buds to produce multiple blooms.
ROOTING HABIT: Very uniform and very fast.
BLOOMING HABIT: The blooming is more predictable than other known varieties, and it is a "9-week" variety.
BLOOMING SEASON: Blooms predictably and in time for Christmas season and well beyond through at least the month of April; is also a good variety for flowering in spring, summer and autumn.
FOLIAGE: The shape of the leaves varies a little from other known varieties.
Shape—Similar to "Annette Hegg."
Color—New foliage—Upper side—Spinach Green, Plate 0960; Lower side—Spinach Green, Plate 0960/2. Old foliage—Upper side—Ivy Green, Plate 0001060; Lower side—Ivy Green, Plate 0001060/2.
BRACTS: Obovate; relatively broad.
Color—Near Carmine, Plate 21/1 to 21.
REPRODUCTIVE ORGANS:
Stamens—Quite numerous; from about ⅛ to ¼ inch long. Color—Currant Red, Plate 821/2.
Pollen—Color—Canary Yellow, Plate 2.
Styles—Color—Currant Red, Plate 821/2.
Ovaries—Color—Scheele's Green, Plate 860.
Nectar cups—Color—Buttercup Yellow, Plate 5/1.

I claim:

1. A new and distinct variety of poinsettia plant, substantially as herein shown and described, characterized particularly as to novelty by the unique combination of a general similarity in most respects to the variety "Dark Red Annette Hegg" (Plant Pat. No. 3,160), including a short growing and compact plant habit, a uniform and fast rooting habit, a self-branching habit which produces multiple blooms without pinching off the terminal buds, attractive green foliage, distinctive, attractive and stable dark pink bracts instead of dark red bracts like "Dark Red Annette Hegg," and long-lasting plant qualities.

No references cited.

ROBERT E. BAGWILL, Primary Examiner